United States Patent [19]

Russell

[11] Patent Number: 4,554,158

[45] Date of Patent: Nov. 19, 1985

[54] MODIFIED LIVE SENDAI VIRUS VACCINE FOR ADMINISTERING THROUGH AN AEROSOL AND METHOD OF PRODUCING THE SAME

[75] Inventor: James D. Russell, Gilroy, Calif.

[73] Assignee: Simonsen Laboratories, Inc., Gilroy, Calif.

[21] Appl. No.: 482,899

[22] Filed: Apr. 7, 1983

[51] Int. Cl.$^4$ .......................... A61K 39/12; C12N 7/08
[52] U.S. Cl. ....................................... 424/89; 435/237
[58] Field of Search ................... 424/89; 435/235, 237, 435/238

[56] References Cited

U.S. PATENT DOCUMENTS

| | | | |
|---|---|---|---|
| 3,420,934 | 1/1969 | Ackerman | 424/89 |
| 3,674,861 | 7/1982 | Churchill | 424/89 |
| 3,869,547 | 3/1975 | Mebus et al. | 424/89 |
| 3,981,771 | 9/1976 | Sevoian | 424/89 |
| 4,029,763 | 6/1977 | Kilbourne | 424/89 |
| 4,053,583 | 10/1977 | Gits et al. | 424/90 |
| 4,195,076 | 3/1980 | Fontanges | 424/43 |

FOREIGN PATENT DOCUMENTS 57-95917  6/1982  Japan ...................................... 424/89

OTHER PUBLICATIONS

Kimura et al., Arch Virol 61(4): 297–304, 1979.
Maassab, Nature, 213, 612–614, 1967.
Biosis 69(6):37356 (1980).
Advertising literature published by Microbiological Associates–Sendai Vaccine.
Elicitation of Anti-Sendai Virus Cytotoxic T Lymphocytes etc., by Arthur H. Hale et al., Journal of Immunology, vol. 124, No. 2, Feb. 1980, pp. 724–731.
Studies on the Immune Response and Pathogenis etc., by G. Blandford et al., Immunology, 1972, vol. 22, pp. 637–649.
Enhancement of Phospholipid Transfer from Sendai Virus etc., by Kuroda et al., Proc. Natl. Acad. Sci. 1980, vol. 77, pp. 804–807.
Immunoelectrophoretic Study of Sendai Virus Envelope etc., by Gr. Ghyka et al., Rev. Roum, Med.–Virol, 1978, vol. 29, pp. 23–28.
Stimulation of Crytolyptic T Cells by Isolated Viral Peptides etc., by D. P. Guertin et al., Nature, vol. 283, 1980, pp. 308–311.
A T Helper Cell for Anti-Viral Cytotoxic etc., by R. B. Ashman et al., 1979, J. Exp. Med., vol. 150, pp. 1277–1282.
Effects and Mechanism of the interaction etc., by S. E. Tomas, Rev. Roum. Med.–Virol, 1978, vol. 29, pp. 129–139.
Biological Activities of Glycoproteins of HVS etc., by Ozawa et al., 1979, pp. 197–202.

Primary Examiner—Sam Rosen
Assistant Examiner—Sharon P. Foley
Attorney, Agent, or Firm—Jack M. Wiseman

[57] ABSTRACT

Live Sendai viruses are modified in fertile chicken egg embryos to be administered as a vaccine through an aerosol for the immunization of animals against Sendai disease. The live Sendai viruses are diluted by at least thirty-one passages in fertile chicken egg embryos. Twenty passages are at a lower than normal incubation temperature and the remaining passages are at the normal incubation temperature.

11 Claims, No Drawings

MODIFIED LIVE SENDAI VIRUS VACCINE FOR ADMINISTERING THROUGH AN AEROSOL AND METHOD OF PRODUCING THE SAME

BACKGROUND OF THE INVENTION

The present invention relates in general to a vaccine for the immunization of animals against Sendai disease, and more particularly to a modified live Sendai virus vaccine adapted for administration through an aerosol and the method for producing the same.

Sendai virus is one of fifteen to twenty viral agents that affect animals. Sendai is a para myxovirus, parainfluenza type I. It produces a respiratory disease characterized by labored respiration, chattering and variable mortality. For laboratory animal producers, Sendai infection is a serious, continuous threat. It results in complete losses of litters and production. An outbreak of Sendai disease in a research environment can destroy long term experiments and long term studies.

A Sendai vaccine has been produced and sold by Microbiological Associates of Walkersville, Md. The Sendai vaccine produced and sold by Microbiological Associates is a formulin killed vaccine of chick embryo origin and is administered by inoculation. Thus, each rodent is individually inoculated.

It has been know that forms of viruses have been administered in aerosols in the immunization of infectious bronchitis in poultry and in distemper in mink. Certain livestock viral forms of IBR and mucosal disease are administered through intra nasal application. Vaccines for the treatment of Newcastle disease have been administered through an aerosol.

The patent to Fontanges, U.S. Pat. No. 4,195,076, issued on Mar. 25, 1980, for Process For The Preparation of Hemagglutinin From Viral Sources And Methods of Utilizing Same, discloses that use of viral proteins from cultures of Myxovirus Influenza that can be administered in the form of an aerosol formulation for preventing or treating influenza. The neuraminidase obtained is administered in the form of an aerosol formulation containing an aqueous diluent gaseous propellant. The influenza virus suspension is inoculated in fertilized chicken eggs. The suspension is an influenza virus in buffered physiological saline. After incubation of the chicken eggs, infected allantoic fluid is collected from the chicken eggs.

In the patent to Kilbourne, U.S. Pat. No. 4,029,763, issued on June 14, 1977, for Influenza Vaccine Containing Purified Neuraminidase Antigen and Method of Using the Same, there is disclosed an influenza vaccine which comprises, as an active ingredient, a neuraminidase antigen, which has been isolated from antigenically distinct proteins of the envelope of influenza virus. The vaccine is administered by injection to a human or an animal.

The patent to Gits et al., U.S. Pat. No. 4,053,583, issued on Oct. 11, 1977, for Live Newcastle Disease Virus Vaccines discloses live Newcastle disease virus vaccines, which are administered to chickens in the form of an aerosol. The virus mutant is grown in chicken embryos at a temperature of 26° C. for the incubation period. Allantoic fluid material is harvested for further passages.

An article entitled "Elicitation of Anti-Sendai Virus Cytotoxic T Lymphocytes By Viral and H-2 Antigens Incorporated Into The Same Lipid Bilayer By Membrane Fusion And By Reconstitution Into Liposomes" by Arthur H. Hale, Douglas S. Lyles and David P. Fan was published in The Journal of Immunology, Vol. 124, No. 2, February 1980, pages 724–731. This article describes that the hemagglutinin-neuraminidase and/or fusion glycoproteins of Sendai virus can elicit anti-Sendai virus and that these glycoproteins and H-2 antigens must be within the same membrane liquid bilayer for effective elicitation of anti-Sendai virus and for effective recognition and lysis of target cells by anti-Sendai virus. Inactivated Sendai virus was used to elicit anti-Sendai virus or to render cells susceptible to lysis by anti-Sendai virus.

SUMMARY OF THE INVENTION

Live Sendai viruses are modified in a culture medium to be administered as a vaccine through an aerosol or the like for the immunization of animals against Sendai disease.

A method for modifying live Sendai viruses to produce a vaccine adapted for administration through an aerosol for the immunization of animals against Sendai disease.

A modified live Sendai virus vaccine adapted for administration through an aerosol for the immunization of animals against Sendai disease.

A method of modifying live Sendai viruses in a culture medium to produce a vaccine adapted for administration through an aerosol for the immunization of animals against Sendai disease. The live Sendai viruses are modified in excess of a predetermined number of passages, a percentage of which are at a lower than normal incubation temperature.

By virtue of the present invention, a vaccine for the immunization of animals can now be administered through an aerosol without causing disease, without spreading to uninoculated animals, and without returning through virulence through rapid back-passage in susceptible animals. The administration of a modified live Sendai virus vaccine through an aerosol for the immunization of animals against Sendai disease can reduce the threat of virulent Sendai outbreaks in production colonies. It has the added advantage that large numbers of animals can be immunized with facility, quickly, and with minimal effort in the face of an active outbreak of Sendai disease.

DETAILED DESCRIPTION OF THE PREFERRED EMBODMENT

ISOLATION OF INITIAL SEEDS OF SENDAI VIRUSES

In the method of the present invention for producing a modified live Sendai virus vaccine adapted for administration through an aerosol, Sendai viruses are isolated to provide initial seeds of Sendai viruses for modification or dilution. In the exemplary embodiment, mice with Sendai virus disease are sacrificed and the lungs thereof are harvested, in the preferred embodiment, into a chilled trypticase soy broth containing 1 mg/ml of crystalline pencillin. The concentration of lungs to broth, in the preferred embodiment, is approximately a ratio of one part lung to nine parts broth. Thereupon, the harvested lungs are minced and are homogenized in a Waring blender. In the exemplary embodiment, the homogenized lungs and broth are centrifuged at 3000 r.p.m. for ten minutes. The supernatant of the centrifuged lungs and broth is collected and dispensed into 1 dram vials and frozen at −21° C. or at a lower temperature. The foregoing provides the initial seeds of live Sendai viruses.

While trypticase soy broth is preferred, it is apparent that any nutrient broth can be utilized. A plain saline or sterile water can be used. Trypticase soy broth is preferred, since it includes both a protein and a sugar which protects the virus during manipulations, thereby increasing chance of recovery. Any antibiotic can be used or can be used in combination with the above ingredients.

Preferably, a ten percent suspension of lung tissues in the trypticase soy broth is used for the recovery of the Sendai viruses. A range of 1% to 50% suspension of lung tissues in the trypticase soy broth may be permissible. In using a 1% suspension the recovery rate for the Sendai viruses will be reduced because of the dilution factor. The 50% suspension of lung tissues in the trypticase soy broth would be the greatest concentrated level of lung tissue that could be manipulated with facility.

DILUTION AND MODIFICATION OF LIVE SENDAI VIRUSES TO FORM A VACCINE ADAPTED FOR ADMINISTRATION THROUGH AEROSOL

The initial seeds are modified in the following manner to provide diluted live Sendai viruses for producing a vaccine that is adaptable for administration through an aerosol. The frozen virus suspension of lungs and broth is heated into a liquid state and the thawed lung and broth suspension is inoculated into fertile chicken egg embryos. Each fertile chicken egg embryo, in the preferred embodiment, receives 0.1 ml of the thawed lung and broth suspension. A chicken egg embryo may receive a quantity of the thawed lung and broth suspension for inoculation in a range of 0.05 ml to 0.2 ml. In the exemplary embodiment, the fertile chicken egg embryos are nine days old.

The inoculation of the thawed lung and broth suspension into the fertile chicken egg embryos is preferably via an amniotic cavity of the fertile chicken egg embryo for improved recovery of the Sendai viruses. The fertile egg embryos are incubated for 72 hours at 39° C. In the exemplary embodiment, ten fertile chicken egg embryos are inoculated with the thawed lung and broth suspension, and amniotic fluid material is collected from the one surviving chicken egg embryo after the 72 hour incubation period at 39° C. The incubation period at 39° C. may be from 48 to 96 hours. The foregoing constitutes the first blind passage. The incubation temperature of 39° C. is the normal incubation temperature. It is preferred for the growth of the embryo to produce improved yields of viruses. However, a range of 35° C. to 40° C. may be employed.

Thereupon, the amniotic fluid material collected from the surviving chicken egg embryo after the first blind passage is inoculated into an amniotic cavity of fertile chicken egg embryos. In the exemplary embodiment, the fertile chicken egg embryos are nine days old. Each fertile chicken egg embryos receives, in the preferred embodiment, 0.1 ml of the amniotic fluid material collected from the surviving chicken egg embryo. The quantity of amniotic fluid inoculant for each embryo may be in the range of 0.05 ml to 0.2 ml. The fertile chicken egg embryos are incubated for 72 hours at 39° C. The incubative period at 39° C. may be from 48 to 96 hours. After ten fertile chicken egg embryos are incubated for 72 hours at 39° C., amniotic fluid material is collected from one surviving chicken egg embryo. The foregoing constitutes the second blind passage. The incubation temperature of 39° C. is the normal incubation temperature. However, a range of 35° C. to 40° C. may be employed. The incubation temperature of 39° C. is preferred for the growth of embryos to produce improved yields of viruses.

Eight additional blind passages are made using the procedures above described. At this time, there are ten blind passages for diluting the live Sendai viruses. The amniotic fluid material containing Sendai viruses for the tenth blind passage is diluted, in the preferred embodiment, in 1:10 in physiological buffered saline containing 1 mg/ml Ampicillin. Other diluents may be employed, such as trypticase soy broth. Other antibodies can be used, such as crystalline pencillin. While amniotic fluid may be used undiluted, it would be rather viscous. The dilution of the amniotic fluid in physiological buffered saline containing 1 mg/ml Ampicillin may be in the range of 1:1 to 1:100. While improved recovery of Sendai viruses can be had from the amniotic cavity, it is apparent that the inoculation into fertile embryos can be accomplished in other wellknown manners.

For further modification and dilution of live Sendai viruses, the fluid material diluted in buffered saline containing 1 mg/ml Ampicillin is inoculated into the allantoic cavity of fertile chicken egg embryos after ten passages. In the preferred embodiment, 0.1 ml of fluid material from the tenth blind passage buffered in saline containing 1 mg/ml Ampicillin is inoculated into the allantoic cavity of fertile chicken egg embryos for the eleventh passage. In the exemplary embodiment, the fertile chicken egg embryos are 12 days old. After the fertile chicken egg embryos are inoculated with the fluid material diluted in buffered saline containing 1 mg/ml Ampicillin, the fertile chicken egg embryos are incubated at 30° C. for 72 hours. The incubation period at 30° C. may be from 48 to 96 hours. While the range of temperature for the cold strain could be between 25° C. to 35° C., temperatures below 28° C. may result in embryo mortality and the embryo could cease to develop. The temperature for the incubation is below normal to provide a cold strain of live modified Sendai virus fluid.

A chicken egg embryo may receive a quantity of fluid material from 0.05 ml to 0.2 ml. The dilution of amniotic fluid in buffered saline containing 1 mg/ml Ampicillin may be in the range of 1:1 to 1:100. While the best recovery of Sendai viruses can be had from the amniotic cavity, it is apparent that the inoculation into fertile embryos can be accomplished in other wellknown manners. Other diluents may be employed, such as trypticase soy broth. Other antibiotics can be used, such as crystalline pencillin. While amniotic fluid may be used undiluted, it would be rather viscous.

In the exemplary embodiment, there are ten fertile chicken egg embryos. Allantoic fluid material is collected from a surviving chicken egg embryo. The allantoic fluid material so collected is diluted 1:10 in physiological buffered saline containing 1 mg/ml Ampicillin. It has been found that 0.1 ml inoculum produced a mathematically desired quantity of virus particles. Once the virus is adapted to egg embryo culture, the allantoic cavity produced higher yields of viruses or more fluid. Thus, eleven passages have been completed. Nine additional blind passages are made using the procedures above described for the eleventh passage. At this time, there are twenty blind passages for diluting the live Sendai viruses.

At the twentieth passage, the cold (below normal incubation temperature of 30° C.) adapted chicken embryo Sendai virus fluid material has been diluted $10^{-6}$ (1:1,000,000) and the highest dilution inoculated, in the exemplary embodiment, into fertile 12 day old chicken egg embryos. The modified Sendai virus containing allantoic fluid material is diluted in physiological buffered saline containing 1 mg/ml Ampicillin. In the preferred embodiment, 0.1 ml of the dilution is inoculated into the allantoic cavity of fertile 12 day old chicken egg embryos.

It has been found that 0.1 ml inoculum produces a mathematically desired quantity of virus particles. Once the virus is adapted to egg embryo culture, the allantoic cavity produces higher yields of viruses or more fluid.

After the fertile chicken egg embryos are inoculated, the fertile chicken egg embryos are incubated for 72 hours at 30° C. (which is a below normal incubation temperature) for the twenty-first blind passage. The incubation period may be between 48 to 96 hours. While the range of temperatures for the cold strain could be between 25° C. to 35° C., temperatures below 28° C. may result in embryo mortality and the embryo will cease to develop. The allantoic fluid material is harvested from the surviving chicken egg embryo. The Sendai virus containing allantoic fluid material is diluted in physiological buffered saline containing 1 mg/ml Ampicillin. In the preferred embodiment, 0.1 ml of the dilution is inoculated into the allantoic cavity of fertile 12 days old chicken egg embryos. It has been found that 0.1 inoculum produced a mathematically desired quantity of virus particles. Once the virus is adapted to egg embryo culture, the allantoic cavity produced higher yields of virus or more fluids. Nine additional blind passages are made using the procedures above described for the twenty-first passage. At each passage, allantoic fluid material is diluted $10^{-6}$ times and the highest dilution is used for the succeeding passage.

The dilution factor of $10^{-6}$ depends upon the titer, which is determined by egg titration. It is desired to dilute fluids to a point in which egg embryos are inoculated with 10 to 30 virus particles for each successive egg embryo passage. This procedure selects the virus particle quantity preferably adapted to cold temperature and egg dilution. In addition, it dilutes for extinction wild or virulent virus particles. Diluting to $10^{-6}$ leaves approximately 30 virus particles per passage per 0.1 ml inoculant. The egg titer would approach $10^{7.3}$ per 0.1 ml of inoculant.

Ten additional blind passages are made using the procedures above described for the twentieth passage. At this time, there are thirty blind passages for diluting or modifying the live Sendai viruses. The allantoic fluid material from the thirtieth blind passage is diluted 1:10 as above described for the twentieth blind passage and inoculated, in the exemplary embodiment, into twelve dozen fertile 12 day old chicken egg embryos. The fertile chicken egg embryos after the thirtieth blind passage are incubated for 72 hours at 39° C. (normal incubation temperature). The incubation period may range from 48 to 96 hours. The preferred normal incubation temperature is 39° C. The range of 38° C. to 40° C. may be employed. After the incubation period of 72 hours, the allantoic fluid material from the thirty-first blind passage is harvested.

In the exemplary embodiment, approximately 250 ml of allantoic material is harvested after the thirty-first blind passage. The allantoic fluid material harvested after the thirty-first passage is, in the exemplary embodiment, dispensed in dram vials. Each vial contains 2 ml of allantoic fluid material. The vials containing the allantoic fluid material are frozen at $-70°$ C. The allantoic fluid material frozen at $-70°$ C. serves as the Sendai virus seed pool. The quantity of 250 ml of allantoic fluid is by way of example in that the quantity may be any convenient amount. The freezing of the allantoic fluid may be in the range of $-20°$ C. to $-80°$ C.

While fertile embryonic chicken eggs are employed, in the preferred embodiment, as the culture medium for the growth of the Sendai viruses, it is well-known from the state of the art that tissue cultures may also be employed as a suitable culture medium for the growth of Sendai viruses.

From the foregoing, it is to be observed that a field isolate of virulent Sendai virus was adapted for growth in fertile chicken egg embryos by 10 blind passages and further modified through 20 passages at suboptimal cold temperature at 30° C. using endpoint dilutions as inoculum for the ten additional passages. It is to be further observed that after 20 additional passages at normal temperature of 39° C. for incubation, a total of 50 blind passages from the original isolation, the modified Sendai virus is stable and does not revert to the virulent form through rapid back passage in susceptible mice nor does it spread from vaccinated animals to unvaccinated contact controls. The modified Sendai virus has adapted to chick embryo culture to produce yields in the range of $1 \times 10^{8.3}$ E.i.d./50 per ml. In the preferred embodiment, the number of blind passages from the time of original isolation of the Sendai virus should exceed thirty-one.

TESTS CONDUCTED DURING THE DILUTION AND MODIFICATION OF A FIELD ISOLATE OF SENDAI VIRUSES

Amniotic fluid material harvested from the one surviving chicken egg embryo after the tenth blind passage was tested for hemagglutination with guinea pig red blood cells. The HA activity was 1600 units/ml. A serum neutralization test with known positive Sendai antisera was performed to demonstrate that Sendai virus had propagated in the fertile chicken egg embryos. Further serum neutralization tests ruled out presence of any other known murine virus contaminants. Amniotic fluids were cultured for absence of mycoplasma or other bacterial contaminants in appropriate conventional media well-known in the art.

At the end of the twenty blind passages, the HA titer of the allantoic fluid material was 128,000 units/ml. The virus containing allantoic fluid material was again tested against known Sendai antisera for purity and titer. The chick embryo infective dose 50 (E.i.d./50) was calculated to be $1.0 \times 10^{7.2}$/ml.

After the thirty-first passage, groups of Sendai disease free mice were inoculated with undiluted egg embryo allantoic fluid material. Ten mice per group were inoculated intraperitoneally, subcutaneously, intracularly, intranasally and per os with 0.1 ml of allantoic fluid material containing 3,000,000 E.i.d./50 of the modified Sendai virus of the present invention. A group of ten mice from the same source served as uninoculated controls. All mice were observed for three weeks for any signs of Sendai infection. All mice remained clinically normal through the observation period.

Serum was collected from all groups and tested for development of protective antibodies using the hemagglutination inhibition test. Those mice inoculated intraperitoneally, subcutaneously and intranasally developed detectable antibody titers. Those mice exposed per os and the uninoculated controls remained negative. All groups were then challenged with virulent Sendai virus (0.1 ml of 10% lung suspension hereinabove described as the initial seeds) intranasally. All mice from the intraperitoneally, subcutaneously and intranasally inoculated groups remained clinically normal through the three week postchallenge observation period. The ten control mice and those administered the modified virus per os became sick and exhibited typical signs of Sendai infection within 4–9 days postchallenge. Thus, the modified Sendai virus which had been passed through thirty-one passages in chicken egg embryos, 20 passages of which were at a cold incubation temperature of 30° C., were safe and effective as a Sendai vaccine.

MODIFIED LIVE SENDAI VIRUSES FOR ADMINISTRATION THROUGH AN AEROSOL

A master seed stock of modified live Sendai viruses is harvested, in the preferred embodiment, from the fiftieth passage. However, the master seed stock of modified live Sendai viruses may be harvested after the thirty-first passage. The master seed stock of modified live Sendai viruses is maintained at −70° C. The incubation temperature after the thirty-first passage, in the preferred embodiment, is the normal temperature of 39° C.

An aliquot of master seed stock is thawed at room temperature and 0.2 ml of the modified live Sendai viruses is inoculated into 10 to 12 day old fertile chicken egg embryos via the allantoic cavity. The inoculated chicken egg embryos are then incubated for 72 hours at 39° C. Approximately one hour prior to harvest, trays of fertile chicken egg embryos are removed from the incubator, candled and placed into a −10° C. freezer. After the chilling, the fertile chicken egg embryos are removed from the freezer, dipped in germicide and the shell over the air sac is removed with sterile forceps.

Allantoic fluid material containing the egg propagated virus is aspirated into a sterile chilled flask surrounded by ice. After the collection of the allantoic fluid material, the allantoic fluid material is centrifuged at 3000 r.p.m. to remove particulate matter and blood cells. The clear supernatant is mixed with an equal volume of cold sterile, 50% sucrose solution in buffered physiological saline. The sucrose solution serves as a stabilizing solution. After thorough mixing, the vaccine thus prepared is dispensed into appropriate size containers. High titer yields of the clear supernatant have been diluted as much as 1:10 sucrose solution (1:20 final dilution) without compromising potency, provided that the final dilution of the clear supernatant has a hemagglutinating activity of 4 HA units per 0.01 ml or an egg infective dose greater than $1 \times 10^{3.0}$ per ml. The resulting vaccine is stored at −20° C. before use.

The modified live virus vaccine can be administered by conventional and well-known equipment that aerosolizes a liquid to provide droplets that are in the 0.1 micron to 1.0 micron size. Droplets of this size are dry and will remain suspended in the surrounding atmosphere long enough to be breathed into the respiratory tract of the vaccinated animals. United Laboratories of Middleton, Wis. sells a vaccine atomizer for delivering aerosol particles less than 0.2 microns. Droplets of less than 0.2 microns are desired to prevent the settling of droplets. It has been found that the modified live virus vaccine can be effectively administered as a droplet into the eye or nose. However, the aerosol application is preferred, because it allows for a greater number of animals to be vaccinated simultaneously without the attendant labor of handling individual animals. The aerosol application, in the exemplary embodiment, utilized compressed air of approximately 10 lbs. per square inch.

In the use of the modified live Sendai virus vaccine, for the immunization of mice and rats, a covered cage suitable for mice or rats or a filtered shipping crate containing mice or rats is sprayed with 0.1 ml of aerosolized vaccine. In the exemplary embodiment, it takes approximately 30 seconds with the Gn BH atomizer to deliver 0.1 ml of the modified live Sendai virus vaccine. The cage or shipping crate is left covered for an additional 30 seconds after contact. The dosage of vaccine is calculated to deliver 0.1 ml per cubic foot of space. In the preferred embodiment, an exposure of 0.1 ml per cubic foot of space for one minute of an aerosol containing no less than $1.1 \times 10^{3.5}$ E.i.d./50 of the modified live Sendai virus vaccine is used to provide an immunizing dose. The Gn BH atomizer is sold by United Laboratories of Middleton, Wis. and is used to vaccinate mink for distemper.

TESTS CONDUCTED ON ANIMALS VACCINATED BY MODIFIED LIVE SENDAI VIRUS VACCINE

Mice and rats have been vaccinated by the modified live Sendai virus vaccine of the present invention in a room environment. The rooms were of approximately 5000 cubic feet in size and aerosolized with 500 ml of vaccine using a conventional insecticide type sprayer-fogger. The sprayer-fogger delivered a fine mist. The vaccine was dispensed in approximately 12 minutes. Each room generally contained between 2000–5000 animals. The mice and rats were successfuly vaccinated without adverse effects or complications. The vaccine was demonstrated effective against Sendai virus infection.

I claim:

1. A vaccine for immunization against Sendai disease comprising live Sendai viruses modified and diluted by a first plurality of passages through incubated culture medium for providing a cold strain of live modified Sendai virus fluid, said incubated culture medium being maintained at an incubation temperature in the range between 25° C. and 35° C. to provide a cold strain of live modified Sendai virus fluid, the incubation period for each of said first plurality of passages being in the range between 48 and 96 hours.

2. A vaccine for immunization against Sendai disease according to claim 1 wherein said cold strain of modified Sendai viruses are further modified by a second plurality of passages through incubated culture medium for harvesting, said last mentioned culture medium being maintained at an incubation temperature in the range between 38° C. and 40° C., the incubation period for each of said last mentioned passages being in the range between 48 and 96 hours.

3. A vaccine for immunization against Sendai disease according to claim 2 wherein the number of passages for said first plurality of passages and said second plurality of passages in the aggregate are at least thirty-one.

4. A vaccine for immunization against Sendai disease according to claim 3 wherein said first plurality of passages are approximately twenty for providing a cold strain of live modified Sendai virus fluid.

5. A vaccine for the immunization against Sendai disease according to claim 3 wherein said modified live Sendai viruses are mixed with a stabilizing solution for dispensing.

6. A vaccine for the immunization against Sendai disease according to claim 5 wherein said mixture of modified live Sendai viruses and stabilizing solution has a hemagglutinating activity of substantially 4 HA units per 0.01 milliliters.

7. A method of administering a vaccine for the immunization against Sendai disease comprising the steps of:
(a) providing a vaccine comprising cold strains of modified live Sendai viruses; and
(b) administering said vaccine through an aerosol.

8. A method of administering a vaccine for the immunization against Sendai disease according to claim 7 wherein said vaccine has a hemagglutinating activity of substantially 4 HA units per 0.01 milliliters.

9. A method of administering a vaccine for the immunization against Sendai disease according to claim 8 wherein said modified live Sendai viruses have been modified by passages through incubated culture medium, said incubated culture medium being maintained at an incubation temperature in the range between 25° C. and 35° C. to provide a cold strain of live modified Sendai virus fluid, the incubation period of each of said passages being in the range between 48 and 96 hours.

10. A method of administering a vaccine for the immunization against Sendai disease according to claim 9 wherein said cold strain of modified live Sendai viruses are further modified by a second plurality of passages through incubated culture medium for harvesting, said last mentioned culture medium being maintained at an incubation temperature in the range between 38° C. and 40° C., the incubation period for each of said last mentioned passages being in the range between 48 and 96 hours.

11. A method of administering a vaccine for the immunization against Sendai disease according to claim 10 wherein there has been in the aggregate at least thirty-one of said first plurality of passages and said last-second plurality of passages.

* * * * *